(12) United States Patent
Ferguson et al.

(10) Patent No.: US 11,560,998 B1
(45) Date of Patent: Jan. 24, 2023

(54) HIGHLY EFFICIENT MEDICAL HEADLAMP

(71) Applicant: RIVERPOINT MEDICAL, LLC, Portland, OR (US)

(72) Inventors: John Thomas Ferguson, Portland, OR (US); Ned Nestorovic, Woodinville, WA (US); Jack Schmidt, San Marcos, CA (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 0 days.

(21) Appl. No.: 16/996,437

(22) Filed: Aug. 18, 2020

Related U.S. Application Data (63) Continuation-in-part of application No. 16/742,669, filed on Jan. 14, 2020, now Pat. No. 11,160,632.

(51) Int. Cl.
| | |
|---|---|
| *F21V 11/10* | (2006.01) |
| *F21V 21/084* | (2006.01) |
| *F21V 5/04* | (2006.01) |
| *F21V 7/04* | (2006.01) |
| *F21V 7/24* | (2018.01) |
| *A61B 90/35* | (2016.01) |
| *A61B 90/30* | (2016.01) |
| *F21Y 115/10* | (2016.01) |
| *F21Y 113/13* | (2016.01) |
| *F21W 131/205* | (2006.01) |

(Continued)

(52) U.S. Cl.
CPC .............. *F21V 11/10* (2013.01); *A61B 90/35* (2016.02); *F21V 5/04* (2013.01); *F21V 7/04* (2013.01); *F21V 7/24* (2018.02); *F21V 21/084* (2013.01); *A61B 2090/309* (2016.02); *A61B 2090/502* (2016.02); *F21V 5/008* (2013.01); *F21W 2131/205* (2013.01); *F21Y 2113/13* (2016.08); *F21Y 2115/10* (2016.08)

(58) Field of Classification Search
CPC ......... A61B 1/06; A61B 1/0607; A61B 1/063; A61B 1/0646; A61B 2090/309; A61B 90/35; F21V 11/10; F21V 21/084; F21V 2131/20; F21V 2131/205
See application file for complete search history.

(56) References Cited

U.S. PATENT DOCUMENTS 5,774,271 A * 6/1998 Lagerway ............... F21L 14/00
359/649
8,047,684 B2 * 11/2011 Chang ................... F21V 14/065
362/268

(Continued)

*Primary Examiner* — Leah Simone Macchiarolo
(74) *Attorney, Agent, or Firm* — Timothy E. Siegel Patent Law, PLLC; Timothy E. Siegel (57) ABSTRACT

A high-efficiency lamp, emitting light from a front surface, and having a high-efficiency light source, producing a first light beam. An iris assembly has an annular body that defines a first annulus and has iris blades which can be extended into the annulus to form a second, smaller, annulus. This iris assembly is positioned relative to the light source so that the iris blades are in front of the high-efficiency light source. The annular body and therefore the first annulus have finite depth from back to front. A light guide is placed immediately behind the iris blades and defines a channel that is open at its back and its front and has a reflective interior surface, with the open back being transversely coincident to the light source so that light from the light source can travel through the channel to and out from the open front.

23 Claims, 7 Drawing Sheets

(51) Int. Cl.
*F21V 5/00* (2018.01)
*A61B 90/50* (2016.01)

(56) References Cited

U.S. PATENT DOCUMENTS

| | | | | |
|---|---|---|---|---|
| 10,107,483 B2* | 10/2018 | Oren | ........................ | F21V 5/008 |
| 10,174,912 B1* | 1/2019 | Ferguson | ................ | F21V 11/10 |
| 10,708,990 B1* | 7/2020 | Ferguson | ................ | A61B 90/30 |
| 2008/0316733 A1* | 12/2008 | Spartano | ................ | F21V 14/06 |
| | | | | 362/105 |
| 2012/0120635 A1* | 5/2012 | Strong | ................... | F21V 5/008 |
| | | | | 362/105 |
| 2014/0334157 A1* | 11/2014 | Ferguson | ................ | F21V 11/10 |
| | | | | 362/277 |

* cited by examiner

HIGHLY EFFICIENT MEDICAL HEADLAMP

RELATED APPLICATIONS

This application is a continuation-in-part of application U.S. Ser. No. 16/742,669 filed on Jan. 14, 2020, which is incorporated by reference as if fully set forth herein.

BACKGROUND OF THE INVENTION

In the design of medical headlamps, it is critically important to avoid wasting light. The more of the light that is produced by the light source, that actually is emitted from the front of the lamp, the longer the battery life per unit of battery charge. Accordingly, a highly efficient headlamp may permit the use of smaller, lighter batteries or permit more time to pass, before the batteries must be changed. Both improvements are highly desirable as reducing battery weight may add to the comfort of the surgeon and increasing time between battery changes reduces an extra set of actions during surgery, which can only serve to complicate an already complicated surgical theater.

Creating a highly efficient headlamp that also permits an adjustment of beam width is a particular challenge, as the iris that is necessary in this type of headlamp, naturally complicates the design and tends to result in some light being blocked or otherwise not being emitted from the front end of the headlamp. It is very difficult to position the light source close to the iris blades, and even if done the light beam will not have spread out as far as is desirable by the time it reaches the iris. But if the light source is positioned behind the iris blades by more than a centimeter, some of the light will be lost.

One factor that increases the cost of producing medical headlamps is the need to make a line of headlamps of several differing designs for different purposes. Typically, each design requires many parts unique to itself, relative to the other headlamps of the line. As a result, the stocking of parts during assembly is greatly complicated, driving up expenses. Moreover, after the purchase of a headlamp it is not possible to easily change its characteristics if a surgeon decides he would prefer a different sort of beam, as an option for a particular sort of surgery.

SUMMARY OF INVENTION

The following embodiments and aspects thereof are described and illustrated in conjunction with systems, tools, and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a high-efficiency medical headlamp, emitting a light beam from a front surface, and having a cylindrical housing, being no greater than 5 cm in diameter and 10 cm long and a high-efficiency light source, supported in the housing, producing a first light beam. A light guide is supported in the housing immediately in front of the high-efficiency light source and defining a channel that is open at its back and its front and having a reflective interior surface, the open back being transversely coincident to the light source so that light from the light source can travel through the channel to and out from the open front. An optical assembly, including at least one refractive lens, is supported in the housing in front of the light guide and having a front surface that is also the front surface of the high-efficiency medical headlamp.

In a second separate aspect, the present invention may take the form of a high-efficiency lamp that emits a beam from a front surface, and having a high-efficiency light source supported in the housing and a light guide supported in the housing immediately in front of the high efficiency light source and defining a channel that is open at its back and its front and having a reflective interior surface, the open back being transversely coincident to the light source so that light from the light source can travel through the channel to and out from the open front, and having a length. Further, an optical assembly, including at least one refractive lens, is supported in the housing in front of the light guide and having a front surface that is also the front surface of the high-efficiency lamp, the optical assembly having a rear surface. Finally, the rear surface of the optical assembly is displaced from the front of the channel by at least the length of the channel.

BRIEF DESCRIPTION OF DRAWINGS

Various embodiments of the invention are disclosed in the following detailed description and accompanying drawings.

DETAILED DESCRIPTION AND EMBODIMENTS

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalent; it is limited only by the claims.

Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

To assist the description of the scope and its components the coordinate terms ["back" and "front"] are used to describe the disclosed embodiments. The terms are used consistently with the description of the exemplary applications and are in reference to the front surface being the surface from which light is emitted.

Figure 1:
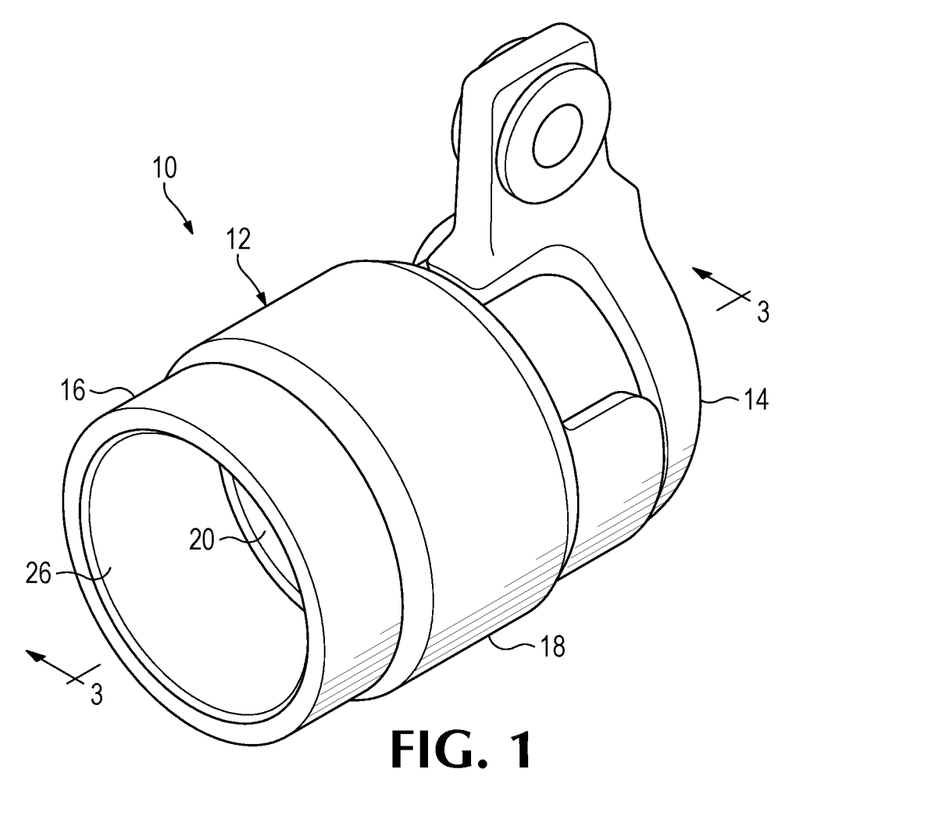
FIG. 1 is an isometric front side view of a lamp, according to the present invention.
Figure 2:
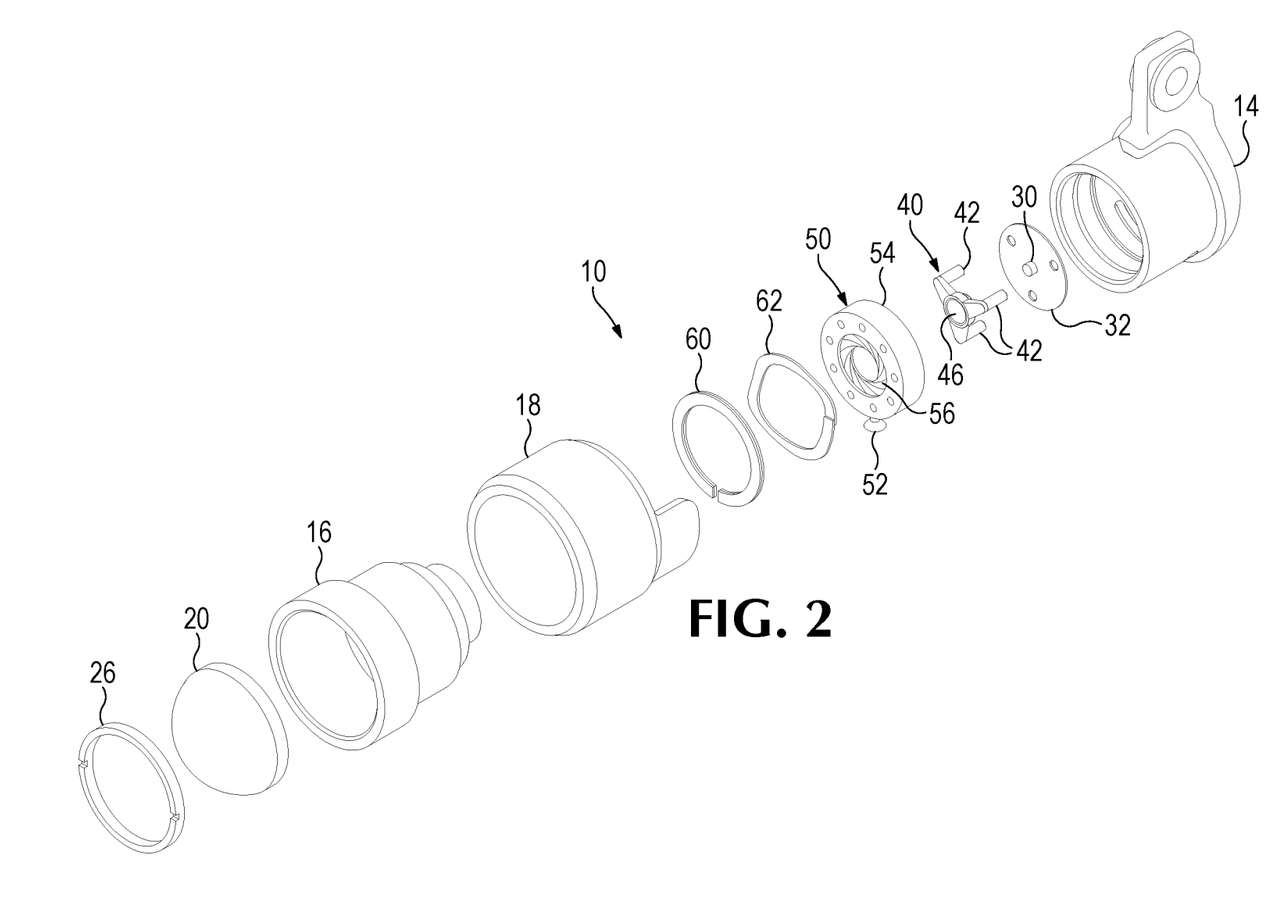
FIG. 2 is an exploded view of the lamp of FIG. 1
Figure 3:
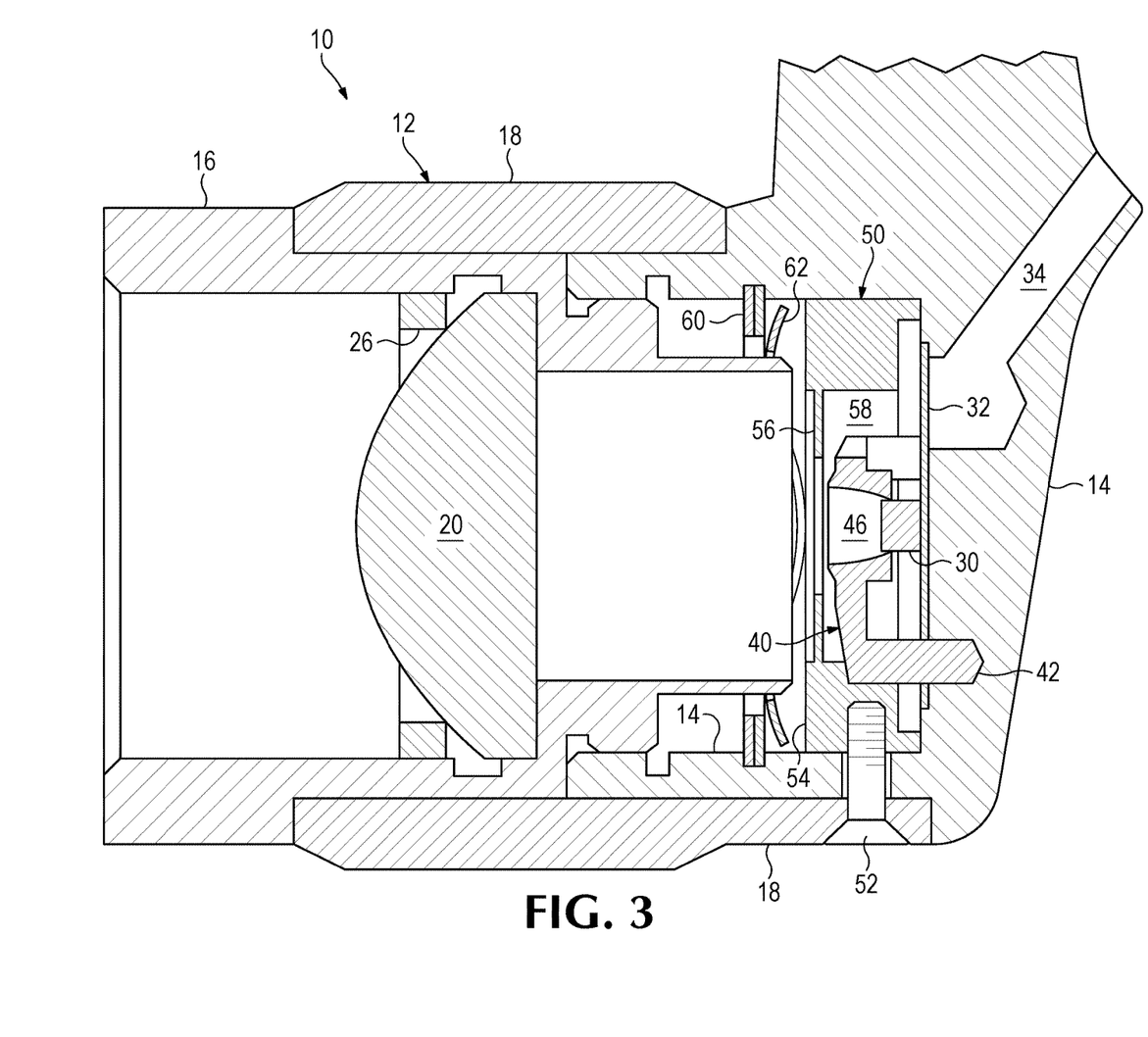
FIG. 3 is a sectional view of the lamp of FIG. 1, taken along line 3-3 of FIG. 1.

Referring to FIGS. 1, 2 and 3, a medical headlamp 10 includes a housing 12, made up of an aft barrel 14, a lens holder 16 and an iris actuation ring 18. Lens holder 16 defines a seat for a single lens 20, constituting an optical assembly and held in place by threaded retainer 26.

Actuation ring 18 can be rotated to change the size of the beam of light emitted and therefore of the spot of light created by the beam. Referring, now, to FIGS. 2 and 3, light is created by a high-efficiency light source in the form of a light emitting diode (LED) assembly 30. A substrate 32 supports LED assembly 30 and supplies it with electricity by way of conductive traces (not shown) and also provides a pathway for heat to travel from LED to housing 12, where it can travel through the metallic housing and radiate out from the housing surfaces. Electricity is delivered to substrate 32 by wires (now shown) extending through a passageway 34 in housing 12. An LED is one example of a high-efficiency light source, defined as any light source that has an efficiency of at least 55 lumens per watt.

A light guide member 40 has three legs 42 that engage with matching holes defined in the aft barrel 14, extending through apertures in substrate 32. Light guide member 40, further includes a light guide 44 that defines a channel 46, open at its front and back, and having a reflective interior surface. In one embodiment, the front of LED assembly 30 extends into the rear portion of channel 46, as shown. In this embodiment, in one variant, the gap between the side surface of LED assembly 30 and the interior surface of the rear end of channel 46 is nowhere greater than 2 mm. In another embodiment, this gap is nowhere greater than 1 mm. In another embodiment, this gap is nowhere greater 0.5 mm. Further, in one embodiment, an iris 50, permits a user to change the width of the light beam that is emitted from the lens 20. An iris actuation pin 52 is engaged to ring 18, permitting a user to adjust the iris by rotating ring 18. Iris blades 56 move inwardly or outwardly from annular housing 54, according to the position of pin 52, creating a smaller or larger light spot. Annular housing 54 defines an annulus 58 (FIG. 3), with blades 56 creating a smaller annulus. Annulus 58 has depth, and light guide 44 fits entirely in it. Placing light guide 44 and therefore channel 46 into annulus 58 brings it close to iris blades 56 prevents a loss of light and creates a more powerful beam than would otherwise be the case. In a preferred embodiment, the front of channel 46 is within 2 mm of the back of the iris blades 56. A pair of washers 60, bracing a wave spring 62, maintain pressure on iris annular housing 54, maintaining its position and preventing it from rotating. In one embodiment, channel 46 is less than 15 mm in diameter at its front end. In an alternative embodiment, channel 46 is less than 10 mm in diameter at its front end. In one embodiment, channel 46 is less than 20 mm long. In an alternative embodiment, channel 46 is less than 15 mm long. In embodiments, the interior surfaces of channel 46 are made of nickel or aluminum. In further embodiments, the interior surface of channel 46 are formed by diamond turning an initial workpiece, made of a highly reflective metal, to produce a precision-shaped interior surface. Although single lens 20 does not create a beam that is as uniform as could be created by multiple lenses, with the addition of light guide member 40, the beam created is acceptable, and the reduction in weight and expense achieved by eliminating a multiple lens train is a positive trade-off for most purposes. In one embodiment, the distance from the back of LED assembly 30 to the front of lens 20 is less than 110 cm. In a preferred embodiment, the rear of lens 20 is separated from the front of channel 46 by a distance at least as great as the length of channel 46. The spot of light created by medical headlamp 10 is a projection of the spot of light that appears at the front of channel 46. In embodiments, the rear surface of lens 20 is 15 mm, 20 mm, and 25 mm in front of the front of channel 46.

Notably, in an embodiment where light guide member 40, or even just light guide 44 is made of a highly thermally conductive metal, such as aluminum, it helps to draw heat away from LED assembly 30, thereby helping to maintain LED assembly 30 at a low temperature, thereby increasing the efficiency of LED assembly 30, which is decreased when the temperature of the LED increases. In embodiments light guide member 30 is constructed with additional legs 42, added fins, and/or protrusions that touch the interior of the housing 12 for the purpose of drawing even more heat away from LED assembly 30. In one embodiment a more powerful LED assembly 30 is used than could otherwise be used because the light guide member draws heat away so efficiently that an LED assembly 30 that produces more heat than could otherwise be tolerated by the system can be used.

The headlamp described above can generally produce more light per unit of power applied to it than previously available headlamps. It is 5 also more compact, thereby reducing total headlamp weight. In a preferred embodiment, the headlamp produces between 130-140 lumens per watt and runs between three and four Watts with a weight ranging from two to four ounces. In one preferred embodiment, bare LED assembly 30 is a Cree® XP-L High Intensity LED.

Figure 4A:
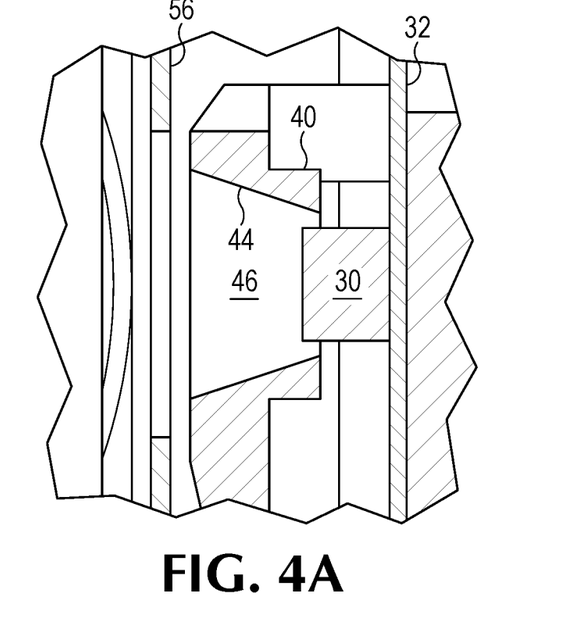
FIG. 4A is a sectional detail view of the light source and light guide of FIG. 3.
Figure 4B:
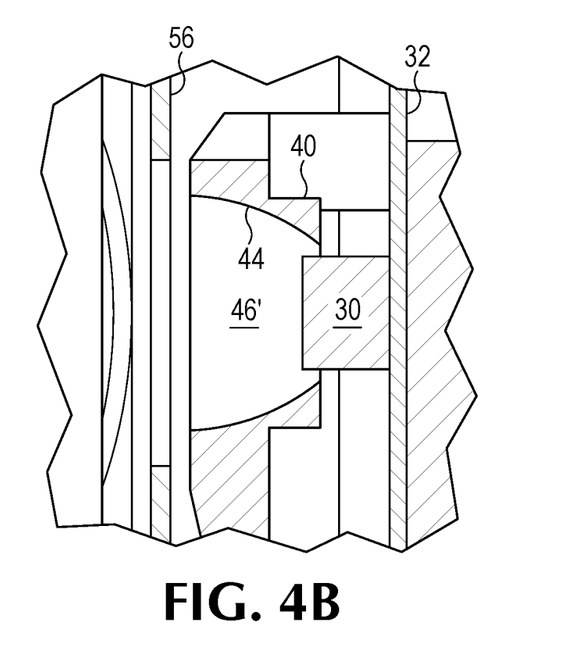
FIG. 4B is a sectional detail of a light source and light guide of an alternative embodiment of a lamp that is otherwise the same as that of FIG. 3.

Referring to FIG. 4A, in a preferred embodiment channel 46 is in the form of a truncated cone. In an alternative preferred embodiment, shown in FIG. 4B, channel 46' is in the form of a parabola section. Other shapes are possible, including a circular cylinder. In a preferred embodiment, channel 46 is transversely circular, but in alternative embodiments channel 46 is transversely a polygon.

Figure 5:
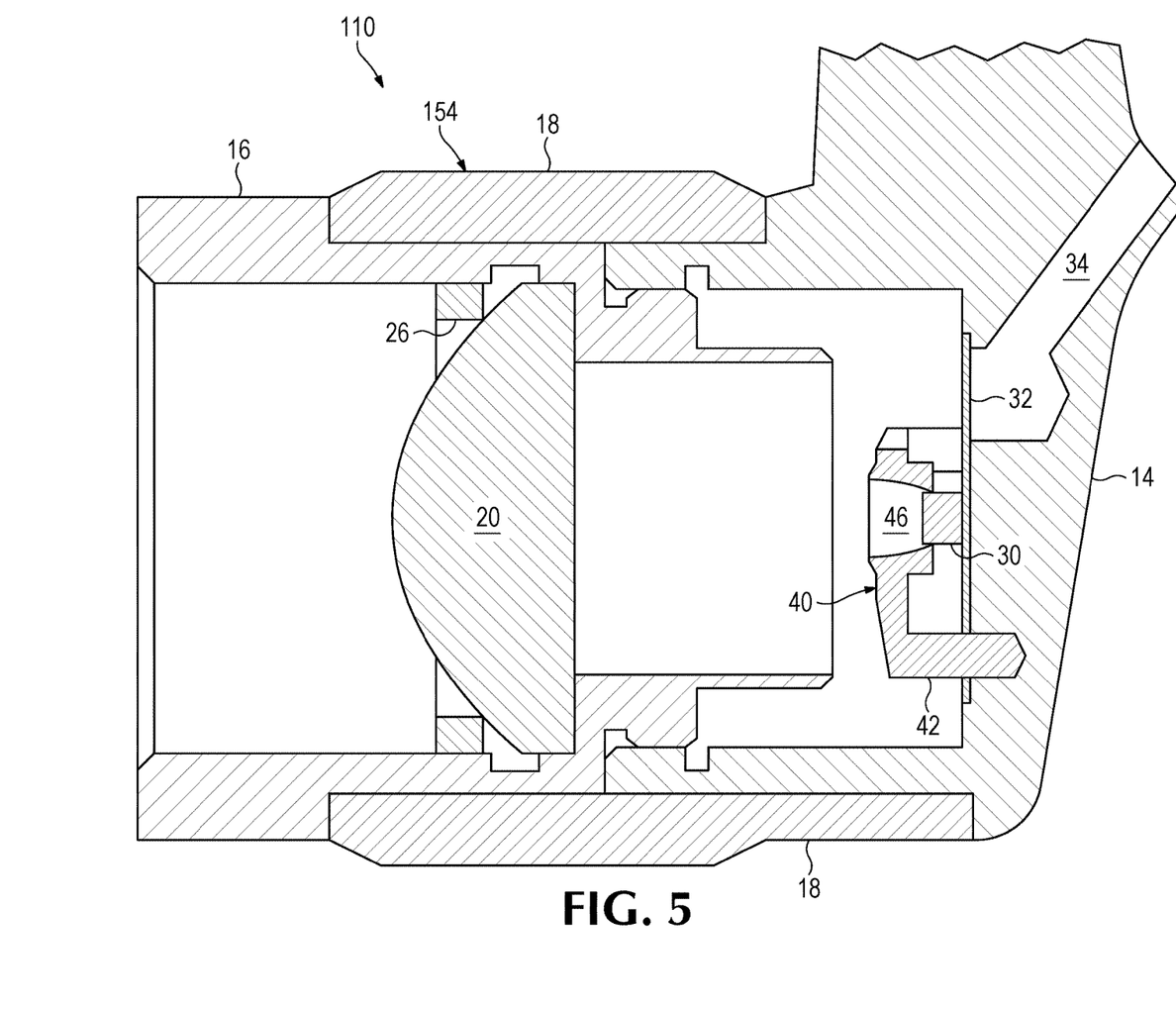
FIG. 5 is a sectional view of an alternative embodiment of a lamp, according to the present invention, which also has the exterior form of the lamp shown in FIG. 1, and wherein the sectional view is taken along line 3-3 of FIG. 1.

FIG. 5 shows an embodiment of a headlamp 110, which has no iris but is otherwise the same as the embodiment of FIGS. 1-3. Where a variable light spot size is not needed or where it is desired to have a lower cost and lower weight lighting solution, the iris may be omitted. In headlamp 110 the housing 154 may be unitary, as there is no need for actuation ring 18 or pin 52.

Figure 6:
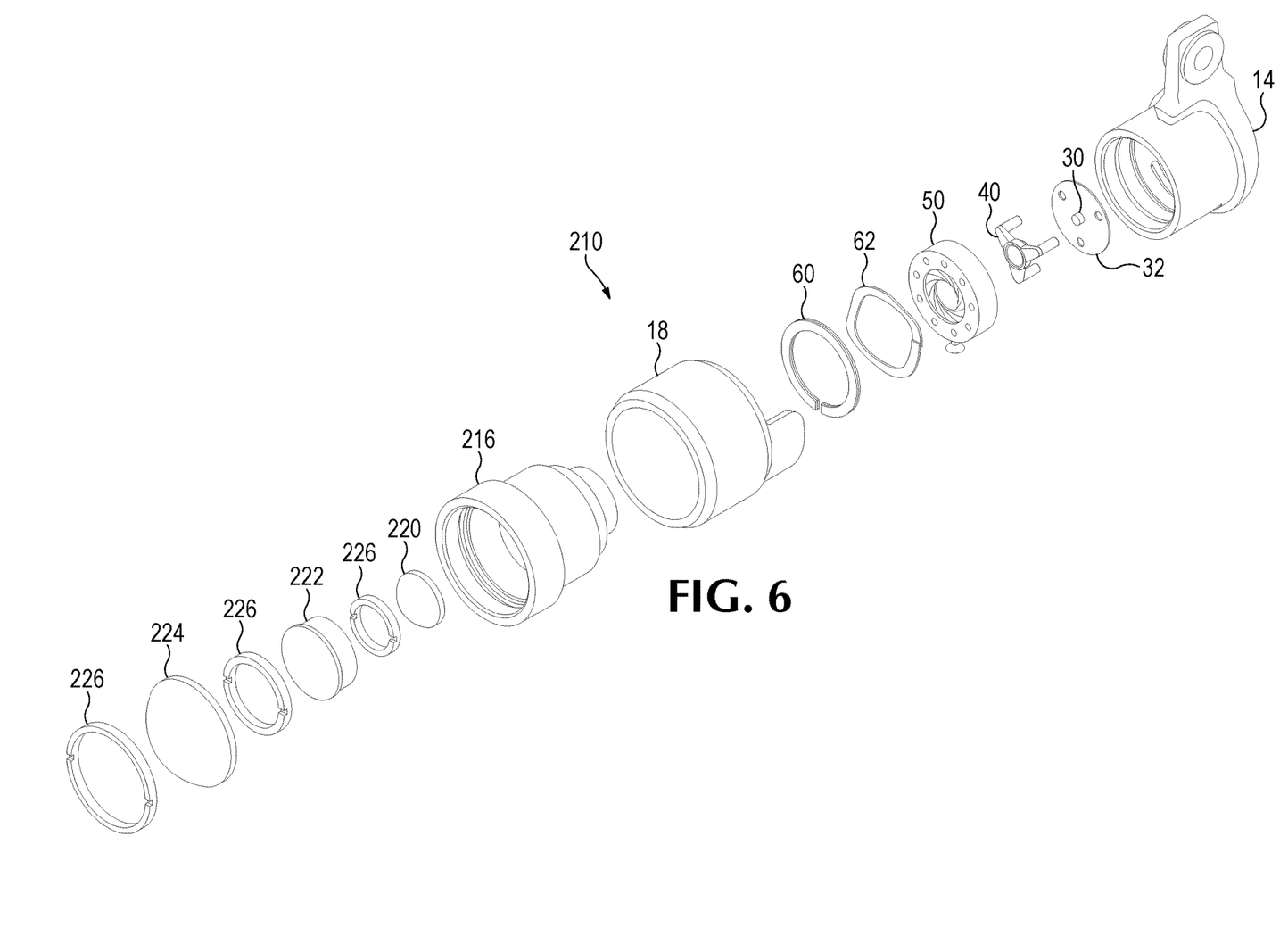
FIG. 6 is an exploded view of an alternative embodiment of lamp, having the same exterior as is shown in FIG. 1.
Figure 7:
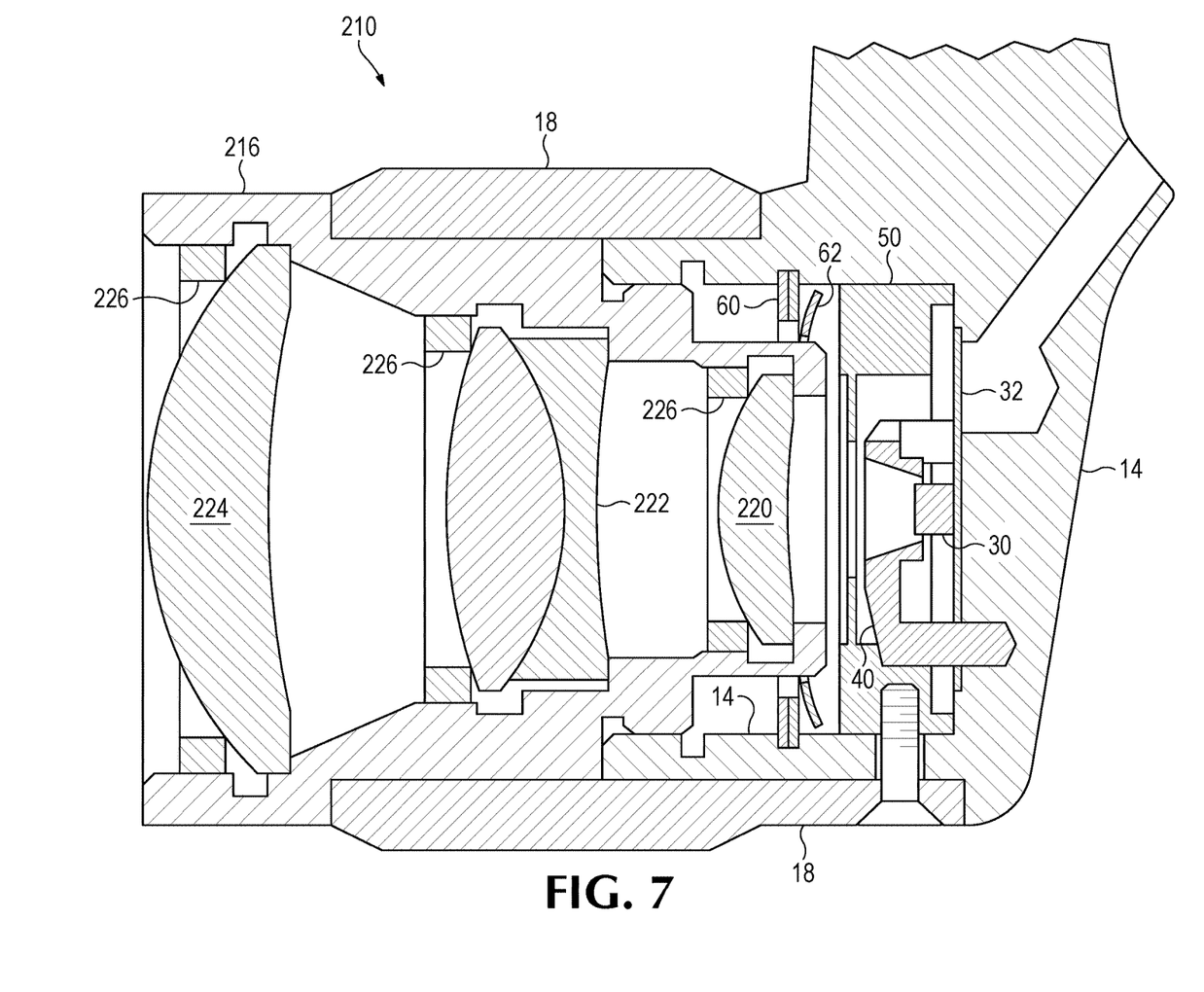
FIG. 7 is a sectional view of the lamp of FIG. 6, taken along line 3-3 of FIG. 1.

Referring to FIGS. 6 and 7 in an alternative embodiment 210, which is otherwise the same as medical headlamp 10, a lens train holder 216 defines circumferential seats for a prime lens 220, an intermediate lens 222, in the form of an achromatic doublet, and a front lens 224. A set of threaded lens retainers 226 screw into threads defined by holder 216 for each lens, thereby for each lens 220, 222 and 224 pressing said lens against its lens seat. For the front lens, this arrangement seals said housing against the intrusion of liquid, for example blood that may shoot out from a patient during an operation, or a cleaning solution used to clean headlamp 210.

An advantage of the configuration of headlamp 10, is that a single design for the optical portion (not including LED assembly 30 or light guide member) can accommodate a wide variety of different LED types. One LED type may be better, emitting light having different characteristics, than another LED type. Both square and round LED dies may be used, with the same optical, front end, design. Further, an LED assembly 30 having multiple LED dies is used in one embodiment. In one embodiment, LED assembly 30 is color tunable. Accordingly, a method of producing headlamps, includes producing optical front ends, of a single design, and back ends including LED dies and light guide members of differing types, with associated supporting elements of a variety of types, and putting a first back end together with the optical front end for a first type of medical headlamp having a first set of characteristics, and then putting a second back end together with the optical front end, to produce a headlamp having a second set of characteristics.

The disclosed embodiments are illustrative, not restrictive. While specific configurations of medical headlamps have been described, it is understood that the present invention can be applied to a wide variety of optical technology. There are many alternative ways of implementing the invention.

What is claimed is:

1. A high-efficiency medical headlamp, emitting a light beam from a front surface, and comprising:
   a) a cylindrical housing, being no greater than 5 cm in diameter and 10 cm long, including an aft barrel and a lens-holder;
   b) a high-efficiency light source, supported in said housing, producing a first light beam; and
   c) a light guide supported in said housing immediately in front of said high-efficiency light source and defining a channel that is open at its back and its front, said channel having a front surface, and having a reflective interior surface, said open back being transversely coincident to said light source so that light from said light source can travel through said channel to and out from said open front;
   d) said lens-holder fittingly engaged to and supported by said aft barrel;
   e) an optical assembly, including at least one refractive lens supported in said lens-holder in front of said light guide and having a front surface that is also said front surface of said high-efficiency medical headlamp and having a rear surface; and
   f) wherein said rear surface of said optical assembly is separated by a gap from a plane aligned to said front surface of said channel, so that light from said light guide is projected onto said rear surface of said optical assembly.

2. The high-efficiency medical headlamp of claim 1, wherein said optical assembly consists of a single refractive lens, only.

3. The high-efficiency medical headlamp of claim 2, wherein said reflective interior surface is made of a material, selected from a group consisting essentially of aluminum and nickel.

4. The high-efficiency medical headlamp of claim 1, wherein said gap is greater than 15 mm.

5. The high-efficiency medical headlamp of claim 4, wherein said channel is less than 10 mm in diameter at said open front.

6. The high-efficiency medical headlamp of claim 1, wherein said channel has a length and wherein said gap is greater than said length.

7. The high-efficiency medical headlamp of claim 1, further including an iris assembly, having iris blades.

8. The high-efficiency medical headlamp of claim 7, wherein said front of said channel extends to within 2 mm of said iris blades.

9. The high-efficiency medical headlamp of claim 1, wherein said high-efficiency light source is an LED assembly.

10. The high-efficiency medical headlamp of claim 9, wherein said LED assembly includes a square LED die.

11. The high-efficiency medial headlamp of claim 9, wherein said LED assembly includes a square die.

12. The high-efficiency medial headlamp of claim 9, wherein said LED assembly is color tunable, producing different colored light according to an input.

13. The high-efficiency medical headlamp of claim 1, wherein said high-efficiency light source has a front portion that is inside said channel.

14. The high-efficiency medical headlamp of claim 1, wherein said channel is transversely round.

15. The high-efficiency medical headlamp of claim 1, further including an iris supported in said housing between said high-efficiency light source and said single lens.

16. The high-efficiency medical headlamp of claim 1, wherein said iris has iris blades and a housing and said housing defines an annulus behind said iris blades and said light guide extends into said annulus.

17. A high-efficiency lamp that emits a beam from a front surface, and comprising:
   a) a housing and a high-efficiency light source supported in said housing;
   b) a light guide supported in said housing immediately in front of said high efficiency light source and defining a channel that is open at its back and its front and having a reflective interior surface, said channel having a front surface, said open back being transversely coincident to said light source so that light from said light source can travel through said channel to and out from said open front, and having a length;
   c) an optical assembly, including at least one refractive lens, supported in said housing in front of said light guide and having a front surface that is also said front surface of said high-efficiency lamp, said optical assembly having a rear surface;
   d) wherein said rear surface of said optical assembly is displaced from a plane aligned to said front surface of said channel by at least said length of said channel, so that light from said light guide is projected onto said rear surface of said optical assembly.

18. The high-efficiency lamp of claim 17, wherein said optical assembly consists of a single refractive lens, only.

19. The high-efficiency lamp of claim 17, further including an iris assembly having iris blades, and wherein said iris blades are placed within 2 cm of said front of said channel.

20. The high-efficiency lamp of claim 17, wherein said channel expands outwardly as it extends from back to front.

21. The high-efficiency lamp of claim 20, wherein said reflective interior surface is made of a material, selected from a group consisting essentially of aluminum and nickel.

22. The high-efficiency lamp of claim 17, wherein said channel has a length and wherein said gap is greater than said length.

23. A high-efficiency medical headlamp, emitting a light beam from a front surface, and comprising:
   a) a cylindrical housing, being no greater than 5 cm in diameter and 10 cm long;
   b) a high-efficiency light source, supported in said housing, producing a first light beam; and
   c) a light guide supported in said housing immediately in front of said high-efficiency light source and defining a channel that is open at its back and its front, said channel having a front surface, and having a reflective interior surface, said open back being transversely coincident to said light source so that light from said light source can travel through said channel to and out from said open front; and
   d) an optical assembly, including at least one refractive lens supported in said housing in front of said light guide and having a front surface that is also said front surface of said high-efficiency medical headlamp and having a rear surface; and e) wherein the rearmost portion of said rear surface of said optical assembly is separated by a gap from a plane aligned to said front surface of said channel, so that light from said light guide is projected onto said rear surface of said optical assembly.

\* \* \* \* \*